United States Patent [19]

Gosciniak

[11] Patent Number: 4,988,501

[45] Date of Patent: Jan. 29, 1991

[54] SUNSCREEN COMPOSITION

[75] Inventor: Donald J. Gosciniak, West Chester, Pa.

[73] Assignee: ICI Americas Inc., Wilmington, Del.

[21] Appl. No.: 495,866

[22] Filed: Mar. 19, 1990

Related U.S. Application Data

[63] Continuation-in-part of Ser. No. 284,539, Dec. 15, 1988, abandoned.

[51] Int. Cl.$^5$ .................... A61K 7/40; A61K 7/42; A61K 7/44; A61K 7/48
[52] U.S. Cl. .................................... 424/59; 424/47; 424/60; 424/78; 514/844; 514/846; 514/847; 514/873; 514/937; 514/938; 514/939; 514/969
[58] Field of Search ............................................ 424/59

[56] References Cited

U.S. PATENT DOCUMENTS

| 4,157,350 | 6/1979 | Wilson et al. | 260/586 R |
| 4,371,651 | 2/1983 | Leistner et al. | 524/178 |
| 4,387,089 | 6/1983 | De Polo | 424/59 |
| 4,489,057 | 12/1984 | Welters et al. | 424/47 |
| 4,562,067 | 12/1985 | Hopp et al. | 424/59 |

FOREIGN PATENT DOCUMENTS 714046  9/1968  Belgium ........................... 524/178

OTHER PUBLICATIONS

Martin et al., JACS, vol. 80, pp. 4891–4895, 1958.
Leistner et al., CA96: 218806w.
Huane et al., CA97: 198653j.
Fenton et al., CA96: 209791k.
Fenton et al., CA94: 218820e.
Pavlisko et al., CA98: 35050s.

*Primary Examiner*—Dale R. Ore
*Attorney, Agent, or Firm*—William E. Dickheiser

[57] ABSTRACT

Sunscreen compositions comprising at least one bis-1,3-diketone derivatives of benzene and a cosmetically acceptable carrier are described. Also disclosed is a method of protecting human skin from the harmful effects of ultraviolet radiation employing such sunscreen composition.

14 Claims, No Drawings

SUNSCREEN COMPOSITION

This application is a continuation-in-part of U.S. patent application Ser. No. 284,539 filed Dec. 15, 1988, now abandoned.

FIELD OF THE INVENTION

This invention is directed to a sunscreen composition comprising at least one bis-1,3-diketone derivative of benzene. In another aspect, this invention is directed to a method of protecting human skin from the harmful effects of ultraviolet radiation employing such a sunscreen composition.

BACKGROUND OF THE INVENTION

The harmful effects of ultraviolet radiation upon human skin are well documented. Exposure to U.V.-B radiation, having a wavelength of 280 to 320 nm can cause sunburn or erythema. Excessive exposure to U.V.-A radiation, having wavelengths in the 320–400 nm range, can lead to rapid aging of the exposed skin or even pathological changes in the skin such as dermatosis.

In order to minimize such exposure, there have been developed cosmetic compositions incorporating compounds having the capacity to absorb ultraviolet radiation in the U.V.-A and U.V.-B ranges. However, many of the compounds currently commercially employed in such sunscreen cosmetic compositions have been found to cause irritation to sensitive skin. Moreover, while certain of these compounds will provide protection, it would nevertheless be desirable to possess sunscreen compositions comprising even more effective ultraviolet absorbing compounds.

While the polymer industry has developed many compounds which will absorb radiation in the critical range which will afford UV-stability to a wide range of materials, unfortunately very few of these compounds are suitable for use in human sunscreen compositions. Specifically, as is noted in U.S. Pat. No. 4,489,057 to Welters et al., at Col. 2, lines 34 et seq., several of the requirements for a U.V. stabilizer for a polymer composition are very different from those for a sunscreen agent for use in cosmetics. Thus, important criteria for cosmetic U.V. absorbers include good U.V. absorption, chemical stability, photostability, odorlessness, colorlessness, good tolerability by skin and mucous membranes, easy processability and good solubility in the solvents or bases commonly employed in the cosmetics industry. In contrast, very different criteria will be important for polymer-protective U.V.-stabilizers, for example, the ability to stop chain reactions in the polymers, with many of the requirements discussed above for cosmetic U.V.-absorbers being irrelevant for polymer use. Accordingly, obtaining U.V.-absorbing compounds suitable for sunscreen applications involves an art which is very different from that relating to polymer-stabilizing U.V. absorbers.

U.S. Pat. No. 4,371,651 to Leistner et al. discloses a broad class of 1,3-dicarbonyl compounds which are shown to enhance the resistance to deterioration by heat and light of polyvinyl halide resins. It has now been found that a narrow class of compounds within the broad disclosure of this patent exhibits desirable sunscreen activity—a finding which is unexpected as none of the members of this class of compounds are included amongst the large numbers of compounds which are identified in such publication as being particularly preferred for the stabilization of polymers against degradation.

SUMMARY OF THE INVENTION

In one aspect, this invention is directed to a sunscreen composition comprising:

(A) a compound having the structure:

$$R-\overset{O}{\overset{\|}{C}}-CH_2-\overset{O}{\overset{\|}{C}}-Z-\overset{O}{\overset{\|}{C}}-CH_2-\overset{O}{\overset{\|}{C}}-R^1 \quad (I)$$

wherein:

R and $R^1$ are each indepedently $C_2$–$C_{10}$ linear or branched alkyl; and

Z is a bivalent phenylene radical having the structure:

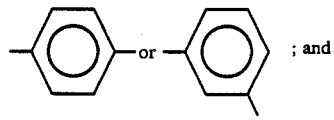
; and (B) a cosmetically acceptable carrier.

In another aspect, this invention is directed to a method of protecting human skin against an overdose of ultraviolet radiation comprising coating the skin with an effective amount of a sunscreen composition comprising:

(A) a compound having the structure:

$$R-\overset{O}{\overset{\|}{C}}-CH_2-\overset{O}{\overset{\|}{C}}-Z-\overset{O}{\overset{\|}{C}}-CH_2-\overset{O}{\overset{\|}{C}}-R^1$$

wherein:

R and $R^1$ are each independently $C_2$–$C_{10}$ linear or branched alkyl; and

Z is a bivalent phenylene radical having the structure:

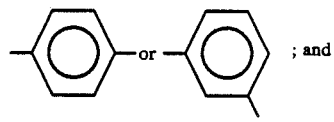
; and (B) a cosmetically acceptable carrier.

DETAILED DESCRIPTION OF THE PREFERRED EMBODIMENTS

This sunscreen composition of this invention is comprised of (A) at least one bis-1,3-diketone derivative of benzene and (B) a cosmetically acceptable carrier.

The bis-1,3-diketone derivatives are of the formula:

$$R-\overset{O}{\overset{\|}{C}}-CH_2-\overset{O}{\overset{\|}{C}}-Z-\overset{O}{\overset{\|}{C}}-CH_2-\overset{O}{\overset{\|}{C}}-R^1$$

wherein:

R and $R^1$ are each independently $C_2$–$C_{10}$ linear or branched alkyl; and

Z is a bivalent phenylene radical having the structure:

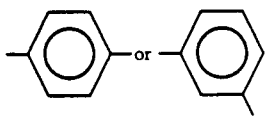

Preferably, R and R¹ are $C_2$-$C_{10}$ branched alkyl and Z is a 1,4-phenylene radical.

More preferably, R and R¹ are $C_3$-$C_9$ alkyl radicals which are branched in the alpha-position. Particularly preferred compositions are those in which R and R¹ are tert-butyl or isopropyl radicals. Such branched radicals are preferred as they exhibit greater solubility in many commercially employed cosmetic bases.

The ultraviolet radiation absorbing compounds employed in the composition of this invention may be prepared in accordance with procedures described in U.S. Pat. No. 4,371,651. Typically, these procedures involve the use of commercially available diesters or the preparation of an aromatic diester by known methods, such as that described by Wals et al. (Rec. Trav. Chem. Pays-Bos, Vol. 87, Pg. 65, 1968), followed by the reaction of such aromatic diester with the appropriate ketone enolate in an inert solvent.

The cosmetically acceptable carriers which may be employed in the composition of this invention include any cosmetic base customarily used for sunscreen agents. The incorporation is carried out by distribution methods customarily used, such as, for example, stirring or homogenizing. Examples of customarily used cosmetics bases are creams, lotions, ointments, solutions, sprays and milks.

Thus, the bis-1,3-diketone compounds described above can be formulated with salve or cream bases to provide fatty or non-fatty light protective salves or skin creams or, by mixing with solvents, possibly adding emulsifiers, liquid light-protection or skin-care preparations.

Suitable solvents include, for example: hydrocarbons, such as solid or liquid paraffin, crystal oil, ceresin, ozokerite, montan wax and the like; vegetable or animal oils, fats and waxes, such as olive oil, mineral oil, carnauba wax, lanolin, spermaceti and the like; fatty acids and esters thereof, such as stearic acid, palmitic acid, oleic acid, glycerol mono- or distearate, glycerol monooleate, isopropyl myristate, isopropyl stearate, butyl stearate and the like; and alcohols such as ethyl, isopropyl, cetyl, stearyl, palmityl, and hexyldodecyl alcohol and the like. Polyhydroxy alcohols, such as glycol, glycerol, and sorbitol, which simultaneously serve as moisturizing agents can also be used.

Other suitable materials include emulsifiers for oil-in-water and water-in-oil systems, such as commercially available non-ionic, cationic or anionic active or amphoteric emulsifiers. Thickening agents, such as methyl, ethyl, or carboxymethyl cellulose: polyacrylic acid; tragacanth, agar agar, and gelatin can also be added. As needed or as desired, additional materials including perfumes, preservatives and/or physiologically compatible coloring materials, may additionally be present.

Preferred cosmetically acceptable carriers are those based on a hydrocarbon or vegetable or animal oil, fat or wax.

In addition to the bis-1,3-diketone compounds, the compositions of the invention can contain one or more additional U.V. absorbers, such as p-methylbenzylidene-D,L-camphor or its sulfonic acid sodium salt, 2-phenylbenzimidazole-5-sulfonic acid sodium salt, 3,4-dimethylphenylglyoxylic acid sodium salt, 4-phenylbenzophenone, 4-phenylbenzophenone-2'-carboxylic acid isooctyl ester, p-methoxycinnamic acid esters, 2-phenyl-5-methylbenzoxazole, p-dimethylaminobenzoic acid esters, 2-hydroxy-4-alkoxy benzophenones and the like.

The bis-1,3-diketone compounds of Formula I are present in the compositions of this invention in a U.V. absorbing effective amount. The exact concentration is not critical and depends substantially on the intended use. Generally, the compositions of this invention contain between about 0.5 and about 15% by weight of compounds of Formula I. In general preferred compositions contain 0.5 and about 8.0% by weight of compounds of Formula I. If the compositions contain additional U.V. absorbers, the total amount of U.V.-absorbing compounds usually varies between about 0.5 and about 15% by weight, preferably between about 0.5 and about 10%.

The method of this invention is accomplished by coating the skin with a sunscreen-effective amount of a sunscreen composition comprising a bis-1,3-diketone compound of Formula I and an acceptable cosmetic carrier. The amount of sunscreen composition required to provide effective protection will vary in accordance with a number of factors, including the sensitivity of the individual being protected, the severity of the ultraviolet radiation, the particular formulation employed, etc. However, one of ordinary skill could easily determine the amount of composition needed t be employed in any given instance.

EXAMPLES

The following Examples are intended to further illustrate the invention and are not intended to limit the scope of the invention in any manner whatsoever.

EXAMPLE 1

Preparation of
1,1'-(1,4-phenylene)-bis-4,4-dimethyl-pentane-1,3-dione
(Compound 1)

To a three-neck 500 ml flask were first added 150 ml of dry tetrahydrofuran, under a nitrogen blanket, followed by the addition of 7.8 grams (0.2 mole) of sodium amide. Pinacolone (10 grams, 0.1 mole) was then added dropwise over 15 minutes and the mixture stirred for an additional 15 minutes. Dimethylterephthalate (9.7 grams, 0.05 mole) was then added and the mixture heated to reflux for 4 hours. The contents were then cooled to room temperature and poured into cold water. The pH was then adjusted to 5.2 with hydrochloric acid. The resulting precipitate was collected by filtration and washed with water. Drying of the solids resulted in isolation of 14.2 grams of material, 91% pure by spectrophotometric analysis. Recrystallization from methanol resulted in pure material (mp=124°–126° C.) having a peak absorption of 342 nm and a molar extinction coefficient of 32,340.

EXAMPLE 2

Preparation of
1,1'-(1,3-phenylene)-bis-4,4-dimethylpentane-1,3-dione
(Compound 2)

A procedure identical to that described in Example 1 was followed except that an equivalent amount of dimethyl isophthalate was employed in place of the dimethyl terephthalate. The recrystallized material exhibited a maximum absorption of 314 nm and a molar extinction coefficient of 30360.

EXAMPLES 3-6 (SYNTHESIS OF COMPOUNDS 3-6)

Following a procedure essentially similar to that described in Example 1, except for the use of various starting materials, four additional compounds within the scope of Formula I were prepared. The structure of these compounds along with their peak absorption and molar extinction coefficients are summarized in Table I below.

COMPARATIVE EXPERIMENTS A, B, and C (Synthesis of Comparative Compounds A, B and C)

Compound A (1,1'-(1,4-phenylene)-bis-4-phenyl-butane1,3-dione)—particularly preferred Compound 1 of Leistner et al; Compound B (1,4-bis (benzoyl-acetyl) benzene—particularly preferred Compound 7 of Leistner et al; and Compound C (2,11-dimethyl-4,6,7,9-tetroxy-dodecane) —within the scope of Leistner et al were prepared in accordance with methods described in this publication. The maximum absorbances and extinction coefficients of these compounds are summarized in Table I.

TABLE I

| Compound | Structure | Color | Maximum Absorbtion (nm) | Extinction Coefficient |
|---|---|---|---|---|
| 1 | (CH$_3$)$_3$C—C(O)—CH$_2$—C(O)—[1,4-C$_6$H$_4$]—C(O)—CH$_2$—C(O)—C(CH$_3$)$_3$ | Clear | 343 | 32,340 |
| 2 | (CH$_3$)$_3$C—C(O)—CH$_2$—C(O)—[1,3-C$_6$H$_4$]—C(O)—CH$_2$—C(O)—C(CH$_3$)$_3$ | Clear | 314 | 30,360 |
| 3 | (CH$_3$)$_2$CH—C(O)—CH$_2$—C(O)—[1,4-C$_6$H$_4$]—C(O)—CH$_2$—C(O)—CH(CH$_3$)$_2$ | Pale Yellow | 343 | 32,313 |
| 4 | CH$_3$—CH(CH$_2$CH$_3$)—CH$_2$—CH$_2$—C(O)—CH$_2$—C(O)—[1,4-C$_6$H$_4$]—C(O)—CH$_2$—C(O)—CH$_2$—CH$_2$—CH(CH$_2$CH$_3$)—CH$_3$ | Clear | 344 | 31,556 |
| 5 | CH$_3$—CH$_2$—C(O)—CH$_2$—C(O)—[1,4-C$_6$H$_4$]—C(O)—CH$_2$—C(O)—CH$_2$—CH$_3$ | Clear | 341 | 28,122 |
| 6 | (CH$_3$)$_2$CH—CH$_2$—C(O)—CH$_2$—C(O)—[1,4-C$_6$H$_4$]—C(O)—CH$_2$—C(O)—CH$_2$—CH(CH$_3$)$_2$ | Clear | 343 | 23,000 |
| A | C$_6$H$_5$—C(O)—CH$_2$—C(O)—C(O)—CH$_2$—C(O)—C$_6$H$_5$ | Green | 365 | 33,810 |
| B | C$_6$H$_5$—C(O)—CH$_2$—C(O)—[1,4-C$_6$H$_4$]—C(O)—CH$_2$—C(O)—C$_6$H$_5$ | Green | 375 | 47,656 |
| C | (CH$_3$)$_2$CH—CH$_2$—C(O)—CH$_2$—C(O)—C(O)—CH$_2$—C(O)—CH$_2$—CH(CH$_3$)$_2$ | Clear | 330 | 21,336 |

The data in Table I shows that several of those compounds which are identified as being particularly preferred UV-stabilizers for plastics by Leistner et al are in fact unsuitable for cosmetic sunscreen applications due to their green color.

EXAMPLE 7

Stability Testing

Several of the compounds of Table I were tested for their irradiation stability by the following method. As a comparison, benzophenone 3, a commercially employed sunscreen, was similarly tested.

The test compounds were dissolved in UV grade methanol (Baker Reagent 9093-03) to a concentration of 10.0 mg/liter. A portion of the solution was placed in a 1 cm path quartz cell and the UV spectra taken with a Beckman DU-6 spectrophotometer. The maximum absorbance was recorded. A portion of the solution was placed in a 150 mm × 18 mm quartz tube and photolyzed for 5-6 hours in a weatherometer (Atlas Electric Devices Co., Model CB 1281) under the following conditions:

temperature: 63° C.
irridation: 0.3 watts/sq cm

The samples were removed periodically and the UV spectra taken as described above. The maximum absorbance was recorded as a function of photolysis time. The percent material remaining as a function of time was calculated by the following formula:

% remaining=Ao/At X 100 wherein:

Ao=maximum absorbance at time=0
At=maximum absorbance at time=T

The results of such testing are summarized in Table II.

TABLE II

| Compound | K (methanol) | Percent Decomposed @ 100 mg/100 ml | @ 1 mg/100 ml |
|---|---|---|---|
| 1 | 98 | stable | <2.0 |
| 2 | 92 | * | * |
| 3 | 104 | 2 | 6.7 |
| 4 | 92 | * | * |
| 5 | 106 | stable | 21.7 |
| 6 | 102 | 4 | 8 |
| A | 47 | 40 | 100 |
| C | 35 | 4.8 | 49.2 |
| Benzophenone 3 | | | |
| max. 323 nm | 45 | 5.5 | 8 |
| max. 287 nm | 68 | 3.2 | 5 |

*Indicates not tested.

The above data show the unexpected stability of the UV-absorbers employed in the sunscreen compositions of this invention relative to a commercially employed sunscreen and other UV stabilizers for polymers disclosed in Leistner et al. (U.S. Pat. No. 4,371,651), thereby indicating that such compounds possess improved properties for sunscreen usage relative to those compounds identified by Leistner et al as being preferred for polymer stabilization.

EXAMPLE 8 AND COMPARATIVE EXPERIMENT D

In order to show the efficacy of the composition of this invention as sunblocks, the following SPF testing was undertaken. A solution comprising 5 weight percent of Compound 3 and 95 weight percent dimethyl isosorbide (DMI) was prepared. This solution was applied to 8 specimens of excised hairless mouse epidermis at a level of 1 mg/cm$^2$ (Example 8). The epidermis was exposed to ultraviolet radiation in the UV-B and UV-A range. As a control, a solution of 100% DMI was tested in equivalent amounts (Comparative Experiment D). The results of such testing are summarized in Table III below.

TABLE III

| Example or Comparative Experiment | SPF Testing | | Standard Deviation | |
|---|---|---|---|---|
| | SPF | | | |
| | UVA | UV-B | UV-A | UV-B |
| 8 | 1.4 | 1.43 | 0.35 | 0.26 |
| D | No Protection | No Protection | — | — |

The above data shows the efficacy of the compositions of this invention as sunblocks.

What is claimed is:

1. A sunscreen composition comprising:

(A) an effective amount of a compound having the structure:

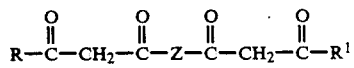

wherein:
R and R$^1$ are each independently C$_2$–C$_{10}$ linear or branched alkyl; and
Z is a bivalent phenylene having the structure

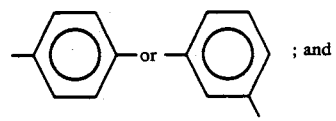

(B) a cosmetically acceptable carrier.

2. A sunscreen composition in accordance with claim 1 wherein Z is a bivalent 1,4-phenylene.

3. A sunscreen composition in accordance with claim 2 wherein R and R$^1$ are each independently C$_3$–C$_{10}$ branched alkyl.

4. A sunscreen composition in accordance with claim 3 wherein R and R$^1$ are each independently C$_3$–C$_9$ alkyl which are branched in the alpha-position.

5. A sunscreen composition in accordance with claim 4 wherein R and R$^1$ are each independently selected from the groups consisting of tert-butyl and isopropyl.

6. A sunscreen composition in accordance with claim 1 wherein said cosmetically acceptable carrier is based upon at least one member selected from the group consisting of the group consisting of hydrocarbon oils, vegetable oils, animal oils, fats and waxes.

7. A sunscreen composition in accordance with claim 1 wherein said composition further comprises an additional UV-absorbing compound in the 280–400 nm range.

8. A method of protecting human skin against an overdose of ultraviolet radiation comprising coating the skin with an effective amount of a sunscreen composition comprising:

(A) A compound having the structure:

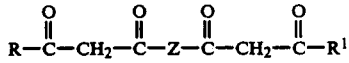

wherein:
R and R$^1$ are each independently C$_2$–C$_{10}$ linear or branched alkyl; and
Z is a bivalent phenylene having the structure:

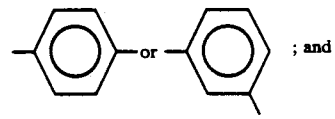

(B) a cosmetically acceptable carrier.

9. A method in accordance with claim 8 of wherein Z is a bivalent 1,4-phenylene.

10. A method in accordance with claim 9 wherein R and R$^1$ are each independently C$_3$–C$_{10}$ branched alkyl.

11. A method in accordance with claim 10 wherein R and $R^1$ are each independently $C_3$–$C_9$ alkyl which are branched in the alpha-position.

12. A method in accordance with claim 11 wherein R and $R^1$ are each independently selected from the group consisting of tert-butyl and isopropyl.

13. A method in accordance with claim 7 wherein said cosmetically acceptable carrier is based upon at least one member selected from the group consisting of the group consisting of hydrocarbon oils, vegetable oils, animal oils, fats and waxes.

14. A method in accordance with claim 7 wherein said composition further comprises an additional UV-absorbing compound in the 280–400 nm range.

* * * * *

UNITED STATES PATENT AND TRADEMARK OFFICE
CERTIFICATE OF CORRECTION

PATENT NO. : 4,988,501

DATED : January 29, 1991

INVENTOR(S) : Donald J. Gosciniak and James P. Neilan

It is certified that error appears in the above-identified patent and that said Letters Patent is hereby corrected as shown below:

On title page, item [19] after "Gosciniak" insert --et al.--; and in item [75] should be changed to read as follows:

-- Donald J. Gosciniak, West Chester, Pa; James P. Neilan, Bear, De. --

Signed and Sealed this

Thirteenth Day of July, 1993

Attest:

MICHAEL K. KIRK

Attesting Officer

Acting Commissioner of Patents and Trademarks